United States Patent
Fletcher

(10) Patent No.: US 10,385,301 B2
(45) Date of Patent: Aug. 20, 2019

(54) MEDIA MIXING CHAMBER

(71) Applicant: IRVINE SCIENTIFIC SALES COMPANY, INC., Santa Ana, CA (US)

(72) Inventor: Thomas Reid Fletcher, Newport Beach, CA (US)

(73) Assignee: FUJIFILM Irvine Scientific, Inc., Santa Ana, CA (US)

( * ) Notice: Subject to any disclaimer, the term of this patent is extended or adjusted under 35 U.S.C. 154(b) by 0 days.

(21) Appl. No.: 16/213,520

(22) Filed: Dec. 7, 2018

(65) Prior Publication Data

US 2019/0106668 A1  Apr. 11, 2019

Related U.S. Application Data

(62) Division of application No. 15/087,826, filed on Mar. 31, 2016, now Pat. No. 10,150,941.
(Continued)

(51) Int. Cl.
*B01F 1/00* (2006.01)
*C12M 1/02* (2006.01)
(Continued)

(52) U.S. Cl.
CPC ......... *C12M 27/00* (2013.01); *B01D 19/0031* (2013.01); *B01F 1/0033* (2013.01);
(Continued)

(58) Field of Classification Search
CPC ............................. B01F 1/0033; B01F 5/0062
(Continued)

(56) References Cited

U.S. PATENT DOCUMENTS 266,081 A   10/1882 Berry
342,998 A   6/1886 Berry
(Continued)

FOREIGN PATENT DOCUMENTS

DE   29813996 U1   10/1998

OTHER PUBLICATIONS

Final Office Action on U.S. Appl. No. 15/087,826 dated Apr. 13, 2018.
(Continued)

*Primary Examiner* — David L Sorkin
(74) *Attorney, Agent, or Firm* — Foley & Lardner LLP

(57) ABSTRACT

A method of reconstituting a powdered cell culture media includes providing a mixing apparatus and providing a powdered cell culture media to the fluid chamber of the mixing apparatus, prior to introducing fluid to the chamber. The method further includes introducing fluid to the chamber through an influent port, wherein the influent port is tangentially oriented relative to an inner wall of the fluid chamber to thereby cause the fluid to follow the wall of the fluid chamber in a circular motion, creating a vortex flow in the fluid chamber by introducing fluid at a sufficient flow rate, and enhancing the vortex flow with a geometric fluid flow aid by further channeling the water around the wall of the fluid chamber, around the geometric flow aid. The method further includes continuing to introduce fluid to the chamber and collecting reconstituted fluid that exits the chamber through the effluent port.

20 Claims, 10 Drawing Sheets

Related U.S. Application Data

(60) Provisional application No. 62/257,685, filed on Nov. 19, 2015.

(51) Int. Cl.
*B01D 19/00* (2006.01)
*C12N 5/00* (2006.01)
*C12M 1/12* (2006.01)
*C12M 1/00* (2006.01)
*B01F 5/00* (2006.01)

(52) U.S. Cl.
CPC .......... *B01F 5/0062* (2013.01); *B01F 5/0071* (2013.01); *C12M 23/14* (2013.01); *C12M 23/28* (2013.01); *C12M 37/02* (2013.01); *C12N 5/0018* (2013.01)

(58) Field of Classification Search
USPC ............ 422/261, 274–279; 366/165.1, 165.2
See application file for complete search history.

(56) References Cited

U.S. PATENT DOCUMENTS

| | | |
|---|---|---|
| 2,451,715 A | 10/1948 | Caldwell |
| 2,636,812 A | 4/1953 | Atkinson |
| 3,261,593 A | 7/1966 | Sharples |
| 3,383,178 A | 5/1968 | Dietz |
| 3,468,633 A | 9/1969 | Honchar |
| 5,232,848 A | 8/1993 | Wolfe et al. |
| 5,470,151 A | 11/1995 | Walthall et al. |
| 6,609,857 B1 | 8/2003 | Hjortstam et al. |
| 10,150,941 B2 * | 12/2018 | Fletcher ................ B01F 5/0062 |
| 2010/0008180 A1 | 1/2010 | Krogh |

OTHER PUBLICATIONS

International Preliminary Report on Patentability in corresponding International Application No. PCT/US2016/046603, dated May 22, 2018, 7 pages.

International Search Report and Written Opinion for PCT/US2016/046603 dated Nov. 15, 2016.

Notice of Allowance on U.S. Appl. No. 15/087,826 dated Aug. 8, 2018.

U.S. Office Action for U.S. Appl. No. 15/087,826 dated Dec. 11, 2017.

U.S. Office Action for U.S. Appl. No. 15/087,826 dated Jul. 10, 2017.

* cited by examiner

MEDIA MIXING CHAMBER

CROSS-REFERENCE TO RELATED APPLICATION

This application is a divisional of U.S. patent application Ser. No. 15/087,826, filed Mar. 31, 2016, which claims the benefit of U.S. Provisional Application Ser. No. 62/257,685 filed Nov. 19, 2015, each of which is incorporated herein by reference in its entirety.

BACKGROUND

Field

Embodiments of the present technology generally relates to mixing apparatus for mixing at least one incoming fluid stream with a material to be mixed with the incoming fluid stream(s). More particularly, embodiments of the present technology relate to mixing apparatus specially adapted for reconstituting powdered cell culture media in predetermined unit volume amounts.

Description of the Related Art

Viable animal cells and tissue in in vitro cultures have been known since the early 1900s. While animal cell culture today is a sophisticated technology, the basic culture technique has not changed since the beginning of the century. Cells or tissue, either primary or transformed, are grown in a liquid nutrient mixture generally referred to as "media." This media can be, for example, a complex mixture of amino acids, vitamins, salts, and other components. It is often supplemented with 1-10% purified bovine fetal or newborn calf serum. Cell culture media and serum are available commercially from many sources.

While the basic cell culture technique has not changed appreciably over the years, the volume of cell culture and the accessibility of this laboratory technique continues to increase dramatically, thereby changing the needs of the cell culture technique. Not only are more research laboratories, pharmaceutical and biotechnology companies employing tissue culture techniques but they are doing so, often, on a relatively large scale. A medical product related corporation may consume tens or hundreds of liters of liquid media a day and employ large numbers of laboratory technicians and scientists to generate antibodies, growth factors or purified protein from tissue culture for commercial use. Thus, between media supply costs and employee time there is a considerable expense associated with the tissue culture process today.

Cell culture media generally is available commercially either as a dry powder which is reconstituted by adding an appropriate volume of water, or as a pre-packaged liquid. There are also a number of additives that are typically added to the media before use. These include sodium bicarbonate, glutamine, additional buffers or antibiotics.

The technology described herein generally relates to improved devices and methods for mixing media in a variety of volumes and circumstances.

SUMMARY

Generally, embodiments described herein relate to devices and methods for powdered media that is easy to prepare, requires less storage space than liquid media, and/or whose preparation requires minimal effort. The technology according to some embodiments relates to mixing apparatus for mixing a material (e.g., a powdered media) with at least one incoming fluid stream. More particularly, some embodiments of the present technology relate to mixing apparatus specially adapted for reconstituting powdered cell culture media in predetermined unit volume amounts, as well as various methods related to the same.

The present technology represents a significant improvement in the technical field.

Some embodiments are based, at least in part, upon some deficiencies and/or inconveniences with existing media technologies, as recognized by the inventors of the instant technology, or based upon the recognition of potential improvements by the inventors.

For example, pre-packaged liquid can be sterile and aliquoted into convenient sizes, and may come ready to use. However, the media is typically light sensitive and has a prescribed shelf-life. Therefore, media must be ordered on a regular basis. It also should be stored under refrigeration and, in its prepackaged form, requires significant man-power time to unpackage and transport. Further, shipping costs of prepackaged liquid is becoming increasingly more expensive.

Furthermore, powdered media is provided in bulk or in premeasured packages. It tends to have a longer shelf life, is less expensive and requires less storage space and handling time than the liquid form. However, the powdered media must be dissolved and aliquoted under sterile conditions. The increased handling and preparation time especially for large volume media preparation often makes pre-packaged liquid media the preferred choice despite the increased cost.

Reconstitution of powdered media generally is a several step process. To prepare a liquid media from a solid powder, a known amount of powder intended for a specific volume of media is measured out and added to a volume of distilled water which is typically slightly less than the final desired volume. The powder and water are stirred until the solid is completely dissolved. A specific quantity of sodium bicarbonate is added and dissolved. The pH may thereafter be adjusted using acid or base and additional water is added to increase the media to its final volume. The entire mixture is then passed through a sterilizing filter. The media may thereafter be collected in a single large sterile vessel, or proportioned into several smaller sterile vessels.

Powdered tissue culture media has a very fine particle size and is hygroscopic. When mixed with water, it has the tendency to "ball" or "clump." Thus, when reconstituting in water or other aqueous liquid, sufficient agitation is required to break up any clumps that may form upon initial contact with water. For smaller batch sizes, sterile magnetic stir bars can be added to the mixing container and the container is then placed on a magnetic stir plate. Additional manipulations usually are required to add stir bars to the mixing containers. In a typical laboratory setting, magnetic stir plates are not a practical solution for large volume media preparation.

In addition, due to its hygroscopic nature, the media absorbs water when stored, especially in humid environments. Wet media has a shortened shelf-life, becomes lumpy and requires aggressive agitation to reconstitute. Thus, powdered media shelf life could be improved if it were provided in premeasured sealed and desiccated aliquots.

The reconstitution process requires several steps and several separate pieces of equipment. It generally requires at least one vessel, large enough to contain the entire final volume of reconstituted media, plus one or more vessels to receive the sterile media after filtration. The sterilized media is usually delivered into open top containers. Thus, most media preparation is done in a laminar flow hood. Processing large volumes of media in a hood is difficult because there is often not enough space to accommodate the containers and sterile media. Some embodiments herein are based upon the recognition that a device that would permit the preparation of large volumes of the product with minimal physical contact and facilitate media preparation without the inconveniences described above would fulfill a long unmet need in the scientific community.

Furthermore, equipment used for reconstitution of powdered media must be thoroughly cleaned between uses to remove residue and eliminate contaminants in the equipment. This requires significant time and even with careful work, the risk of contaminants remain. Thus, some of the embodiments that follow relate to a low-cost equivalent of a media mixing chamber that is constructed for single use.

One embodiment of the technology relates to a mixing apparatus for reconstituting a powdered cell culture media. The apparatus includes at least one fluid chamber, a first influent port at a top portion of the fluid chamber, and a second influent port at a lower portion of the fluid chamber. The apparatus further includes a geometric fluid flow aid positioned in the fluid chamber and an effluent port at the top of the fluid chamber. A powdered cell culture media is provided in the fluid to be mixed with a fluid provided by at least one of the first or the second influent port. The effluent port is configured to allow reconstituted media to exit the fluid chamber.

A second embodiment of the technology relates to a method of reconstituting a powdered cell culture media. The method includes providing a mixing apparatus having at least one fluid chamber, a first influent port at a top portion of the fluid chamber, a second influent port at a lower portion of the fluid chamber, a geometric fluid flow aid positioned in the fluid chamber, and an effluent port at the top of the fluid chamber. The method further includes providing a powdered cell culture media to the fluid chamber, prior to introducing fluid to the chamber, and then introducing fluid to the chamber through at least one of the first and the second influent ports. The first and the second influent ports are tangentially oriented relative to an inner wall of the fluid chamber to thereby cause the fluid to follow the wall of the fluid chamber in a circular motion. The method further includes creating a vortex flow in the fluid chamber by introducing fluid at a sufficient flow rate, and enhancing the vortex flow with the geometric fluid flow aid by further channeling the water around the wall of the fluid chamber, around the geometric flow aid. The method includes continuing to introduce fluid to the chamber and collecting reconstituted fluid that exits the chamber through the effluent port.

BRIEF DESCRIPTION OF THE DRAWINGS

The above-mentioned features, as well as other features, aspects, and advantages of the present technology will now be described in connection with various embodiments of the invention, in reference to the accompanying drawings. The illustrated embodiments, however, are merely examples and are not intended to limit the invention.

FIG. 5b is a bottom perspective view of the top cone illustrated in FIG. 5a.

DETAILED DESCRIPTION

Figure 1:
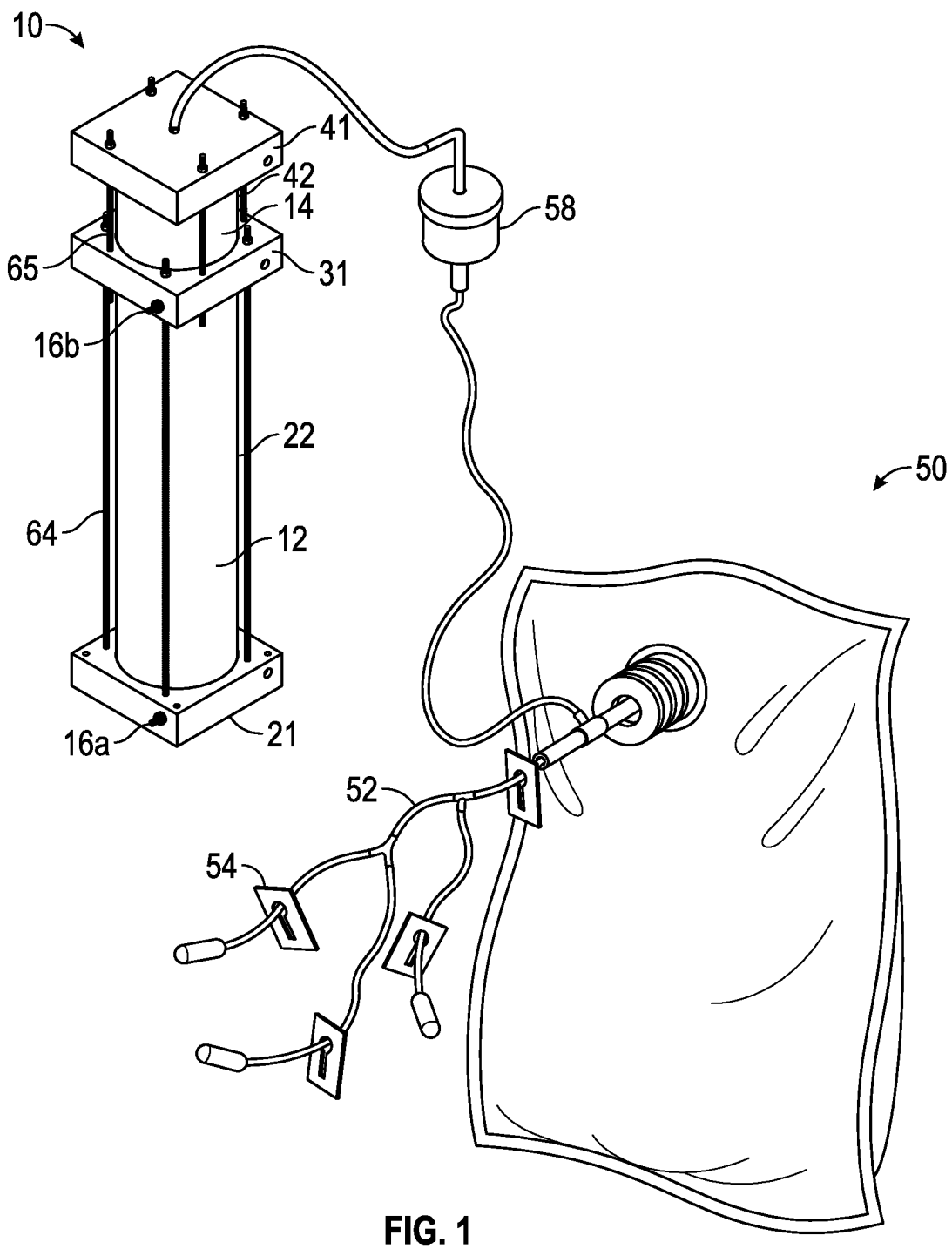
FIG. 1 is a schematic representation of the overall mixing chamber, sterilization filter, and receiving receptacle system in accordance with one embodiment.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. The detailed description is intended as a description of exemplary embodiments and is not intended to represent the only embodiments which may be practiced. The term "exemplary," as used herein, means "serving as an example, instance, or illustration," and should not necessarily be construed as preferred or advantageous over other embodiments. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure.

Embodiments described herein generally relate to devices/apparatuses, systems, and methods related to the storage, transport, preparation and/or use of media, for example, media for cell culture. One or more of the provided embodiments may overcome one or more of the drawbacks, limitations, or deficiencies that exist in the art, particularly with respect to media cartridges and the limitations of such cartridges, including those with dry powder media. For example, in some embodiments, the devices/apparatuses can be single use, disposable, pre-loaded with a desired substance. The devices can include components that permit one of more of improved sterility, storage duration, transport, mixing of materials within the devices, and use of the media. Systems and methods of making and using the devices also are described herein.

Figures 2, 3:
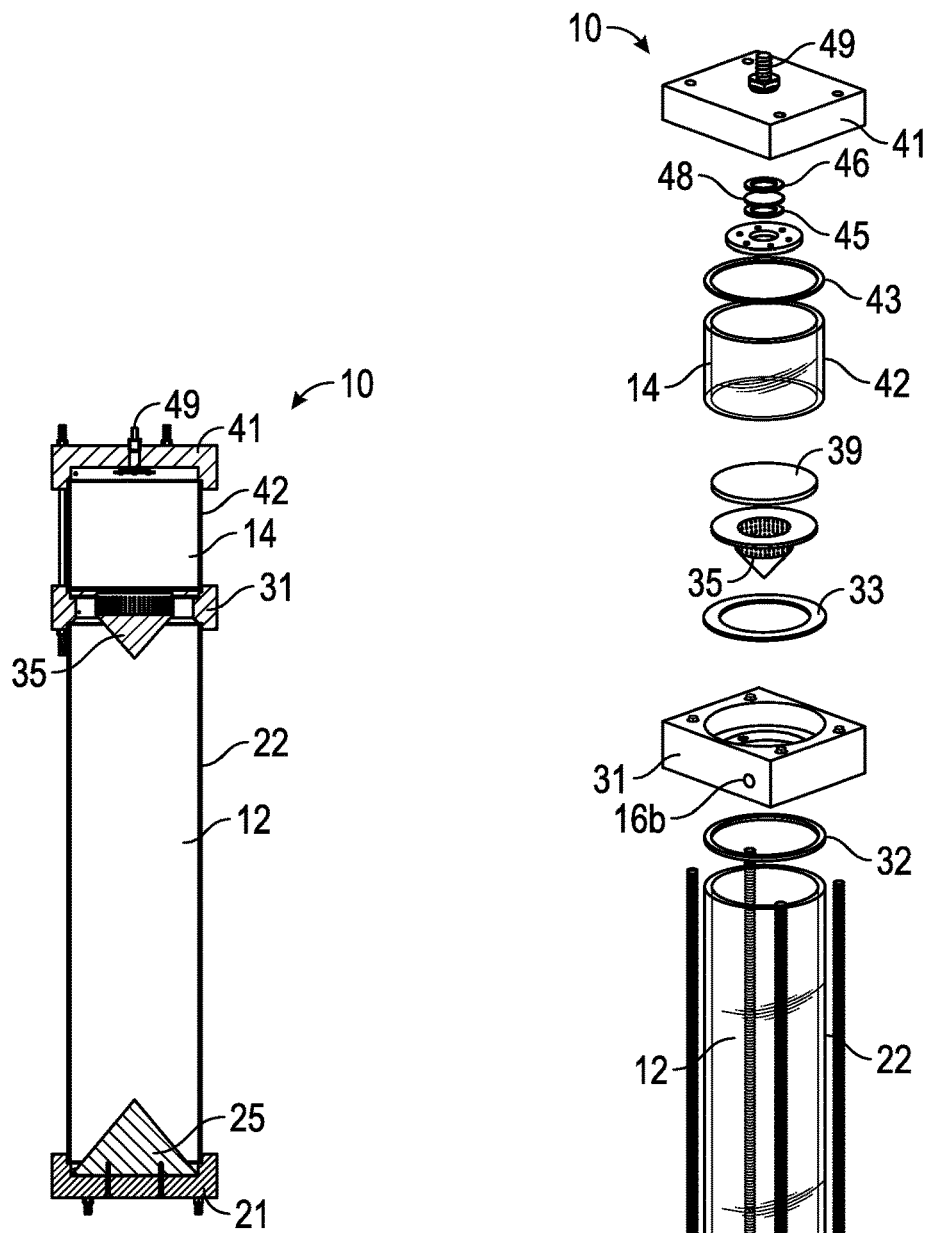
FIG. 2 is a cross-sectional view of the embodiment of the mixing chamber of FIG. 1.
FIG. 3 is an exploded view of a mixing chamber according to a second embodiment.

FIG. 1 is an overall system view of one embodiment of the mixing apparatus 10, filter 58 and receiving bag 50 in accordance with the certain embodiments. FIG. 2 is a cross-sectional view showing an inner view of the components of the mixing apparatus 10. The mixing apparatus 10 comprises at least one, and in some embodiments, two chambers. The generally cylindrical first chamber 12 constitutes the lower chamber in the preferred embodiment depicted herein and a second chamber 14 constitutes the upper chamber of this preferred embodiment. For descriptive purposes "chemical A" will refer herein to the material contained in first chamber 12 and "chemical B" will refer to the material contained in the second chamber 14 in a two chamber embodiment.

An incoming fluid stream enters the mixing apparatus 10 through at least one influent port. It is contemplated that the features of the mixing apparatus 10 described herein are applicable in a mixing apparatus 10 with one influent port, though the application will describe embodiments having a plurality of influent ports, such as the two influent ports 16a, 16b shown in the embodiment of FIG. 1. The axis of the influent port(s) relative to the first chamber 12 can be such that the fluid flow enters at substantially a tangential angle to the interior wall thereof, such that liquid entering the first chamber through influent ports 16a, 16b follows the sides of the chamber to create a circular mixing motion that facilitates mixing of chemical A with the fluid stream within the first chamber. Employing more than one influent port helps direct flow toward the undissolved volume of chemical A, typically present in a solid, powder form. Upper influent port 16b also helps to prevent the solid media from sticking to the top of the first chamber 12. The influent ports 16a, 16b may be used concurrently, or can be alternated to achieve the necessary level of fluid motion for mixing chemical A with the fluid streams.

As chemical A dissolves in the liquid and additional liquid enters into first chamber 12, the liquid level advances upward through middle cap 31 and enters the second chamber 14. Fluid containing chemical A passing through middle cap 31 and entering into the upper chamber now comes in contact with chemical B.

In a preferred embodiment, chemical B has increased solubility characteristics over chemical A such that significant agitation is not necessary to facilitate the dissolution of chemical B in liquid which already contains chemical A.

Figure 9A:
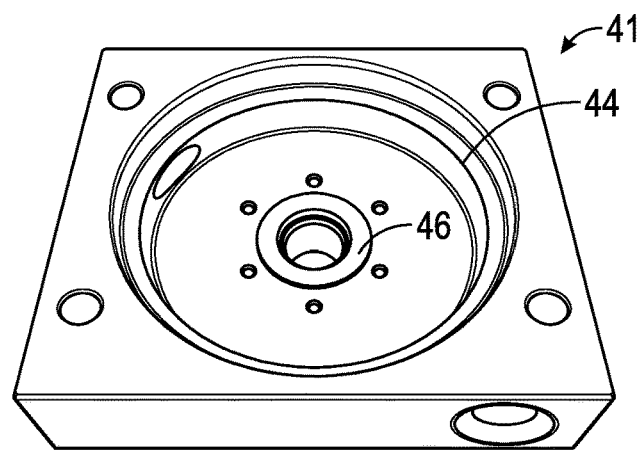
FIGS. 9a, 9b, 9c, and 9d are perspective views of the bottom of a top cap of the mixing chamber according to one embodiment showing the assembly of the top cap.
Figure 9B:
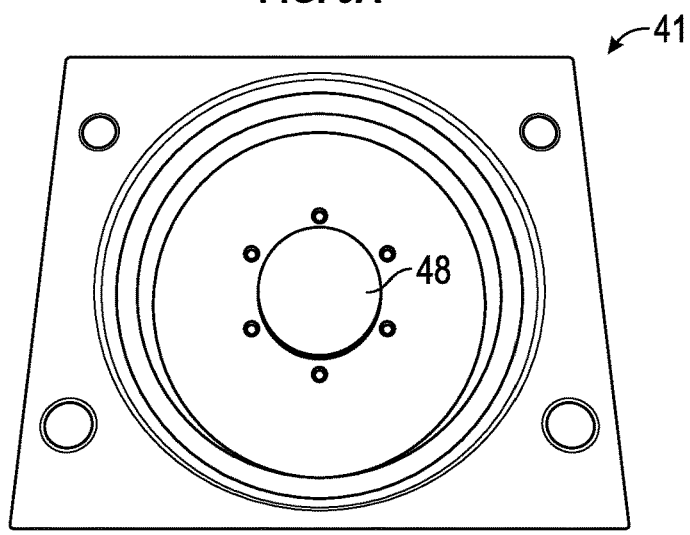

Liquid containing dissolved chemicals A and B thereafter exits second chamber 14 via upper cap 41 through an effluent port 49 preferably after passing through a filter 48 (FIGS. 3, 9B). Liquid passing through effluent port 49 (obscured by tubing in FIG. 1; shown in FIG. 2), in a preferred embodiment, enters into sterilization filter 58. Sterilization filters of the type contemplated by this technology can be purchased from a number of suppliers. One example of a commercial supplier is Pall Corporation, Courtland, Me. For a sterile media product, the sterilization filter apparatus will typically contain a 0.2μ filter. The filter may comprise nylon or cellulose acetate. Sterile liquid containing chemical A and chemical B thereafter exits filter 58 and passes into a receiving receptacle 50. In some embodiments, a hydrophobic vent filter is employed between the effluent port and the sterilizing filter 58 in order to allow the air that is entrained in the dissolved medium to vent so that it does not fill the sterilizing filter.

It is additionally contemplated that other types of filter sizes could be chosen for other functions. For example, the preparation of electrophoretic buffers requires clean, but not necessarily sterile solutions, and a 0.45μ filter would be adequate. Similarly, the preparation of more viscous solutions may necessitate a wider pore size. In short, the filters can be of any desired size, volume, pore size, and so forth, to accommodate the particular use of the cartridge. For other applications of the technology disclosed herein, no filtration apparatus need be added. Liquid then passes directly to a receiving receptacle through any suitable fluid communication device, for example, flexible tubing. If a sterile filter is used, then tubing and all additional chemicals entering multiple inlet ports 52 as well receiving receptacle 50 should be sterile (see FIG. 1).

It is further contemplated that the final product may require the addition of one or more other liquid additives, or the receptacle 50 may be drained into a series of different containers. Therefore, one or more inlet/outlet ports generally designated as multiple inlet/outlet ports 52 are typically provided. Flow stop regulators 54 are preferably associated with each of the inlet ports to provide control for the sequential draining or influx of the desired additive solutions.

FIG. 3 depicts in detail an exploded view of an embodiment of mixing apparatus 10. Mixing apparatus base, or lower cap 21 is combined with first chamber housing 22 in association with a seal 23. A support structure 24 is preferably integrally molded together with or milled into the lower cap 21 to form a ledge or lip to support the first chamber housing 22. The support structure 24 and the first chamber housing 22 are preferably substantially cylindrical in shape to optimize the rotational velocity of the fluid which has been driven through influent port(s) 16 under pressure. The seal 23 is preferably an elastomeric O-ring but could be a gasket or other sealing device known to those with skill in the art. The bottom cap also supports a geometric flow aid, such as bottom cone 25. Assembly of the lower cap 21 is described in more detail below with reference to FIG. 7.

First chamber housing 22 receives the inflowing liquid through one or more influent ports 16 (shown in FIG. 1), generally tangentially oriented to the interior wall of the housing. The one or more influent ports 16 may be integrally molded with the housing 22, or can be affixed thereto in any of a variety of ways known in the art such as by adhesive, solvent or heat bonding techniques. According to the embodiments shown, two influent ports 16 are integrally molded with lower cap 21 and middle cap 31 with a passage allowing fluid flow between the influent ports 16 and the interior of the housing 22. A hose barb or other conventional connector is preferably affixed to influent port 16. Preferably, influent port 16a is located in the lower half of the first chamber 12, and more preferably along the lower one-fourth of the first chamber 12, such as on lower cap 21. Preferably, influent port 16b is located in the upper half of the first chamber 12, and more preferably along the upper one-fourth of the first chamber 12, such as on middle cap 31. In embodiments having a single influent port, the influent port may located in the lower half of the first chamber 12, and more preferably along the lower one-fourth of the first chamber 12, such as on lower cap 21. A protective cap may be provided to cover the influent port(s) thus preventing powder from spilling out prior to use. In some embodiments, quick-connect devices are employed at the influent port so that the quick-connect device prevents the egress of powdered cell culture media powder from the cartridge during storage and shipment.

Fluid entering the second port at a sufficient velocity assists the vortex created by fluid entering from the first port. For the reconstitution of large amounts of dry powder or viscous solutions, two influent ports might better facilitate complete mixing. Thus, water or other solvent could be added from more than one influent port solely to support vortex generation. Alternatively, the liquids entering the apparatus through multiple influent ports could be of different chemical composition.

The influent ports can be positioned on the same vertical plane, as shown in FIG. 1, or along different vertical planes, depending upon particular requirements of a given application, so long as the inflow from port 16a does not interfere with the inflow from port 16b. Fluid tangentially entering the mixing chamber from both ports should flow in tandem to maintain vortex activity.

It is contemplated that influent ports 16a and 16b have equal port diameters. However, the diameters may be individually modified for varied influent flow velocities. The interior diameters of each of the ports and influent pressures can be varied to promote mixing of the desired reagents. A smaller diameter port situated above a larger diameter port would provide additional inflow velocity over the larger diameter port. In this way an efficient vortex could be maintained to maximize reconstitution of a given powder mixture. These design features will be added or included depending on the solubility of the powder in a particular application, the volume of powder relative to the chamber size and by the chemistry required to reconstitute a given liquid preparation.

In use, liquid enters the mixing chamber through influent ports 16a, 16b. Faucet pressure or other inflow pressures in excess of about 1 psi are generally sufficiently strong to permit proper apparatus function. Typical tap pressure, in the area of about 25 psi is sufficient for many embodiments. The minimum effective pressure is a function of the scale of the first mixing chamber, the volume of chemical A contained therein and the diameter of the influent lumen, as will be understood by one of skill in the art. Some routine experimentation may be required to optimize these parameters for specific applications. For example, these parameters may be designed specific to the available water source. When source fluid pressure cannot be increased, the present mixing apparatus may be designed by decreasing the diameter of the inlet.

As previously described, liquid enters the first chamber under pressure at substantially a tangent to the interior wall of the chamber. The velocity of the liquid entering the apparatus is determined by the incoming fluid stream pressure and can be additionally manipulated by altering either the diameter(s) of the influent port(s) or the dimensions of the first chamber. Decreased influent port diameters will increase the velocity of liquid entering the chamber, while increased influent port diameters will decrease liquid velocity. In a preferred embodiment, a sufficient fluid velocity is achieved when the ratio of the cross-sectional area of the influent port through which fluid is entering the chamber (in inches) to flow rate (liters/minute) is 0.0015-0.0040. In some preferred embodiments, the ratio is 0.0018 to 0.0038. In some preferred embodiments, the ratio is 0.0028+/−0.0002 (in other words, 0.0028 square inches for the inlet with 1 liter per minute of fluid flow).

It is contemplated that slight modifications of the apparatus will be required for the proper functioning of the mixing chamber for other applications. For example, if the liquid is water and the product is tissue culture media, then normal faucet pressure, in concert with an appropriate influent port dimension will create sufficient liquid pressure to generate the desired rotational fluid velocity. The mixing chamber influent port diameter has a direct effect on inlet velocity. As noted above, the inlet diameter can be increased or decreased to adjust the velocity in order to provide adequate mixing of the media.

In an embodiment with two influent ports, such as 16a and 16b, it is preferred that fluid is first provided to the chamber through upper influent port 16b, so as to prevent floating of undissolved clumps of powdered media. Once fluid has partially filled the chamber, lower port 16a is open and begins to facilitate a vortex-like fluid flow motion.

Figure 4:
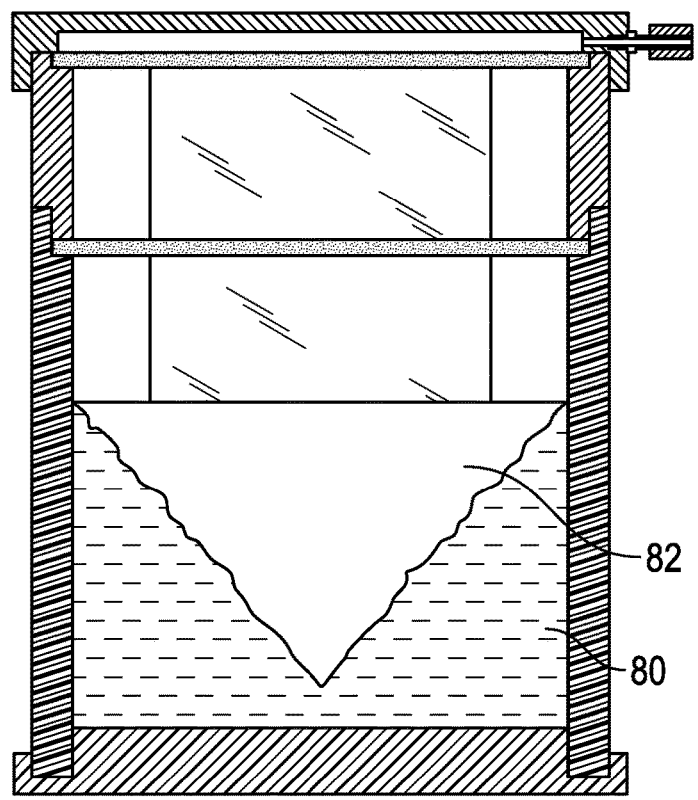
FIG. 4 is a cross-sectional view of a mixing chamber according to the prior art with a representation of a fluid vortex.

Preferably the pressure of the liquid stream in combination with a compatible influent port diameter will provide sufficient liquid velocity such that liquid entering the apparatus follows the surface of the inner chamber casing and continues along a circular pathway towards the center of the chamber. If the rotational fluid velocity of the liquid is sufficient, the motion subsequently establishes a turbulent vortex that serves to mix the influent liquid with the contents of the first chamber. This motion is shown in FIG. 4 representing the desired fluid motion in a prior art mixing apparatus. The dashed horizontal lines 80 represent the swirling fluid that creates a roughly conical region of air 82 at its center. The swirling vortex mixes the contents of the chamber. Additional fluid entering the chamber pushes the vortex up the sides of the chamber and towards the top. Though this vortex motion is anticipated under the right conditions, it is not always achievable now as the powdered solid chemical has changed over time. In many cases, with current media, the vortex flow does not occur, and the entering fluid simply pours into the chamber. In these situations, without proper agitation, the powdered media contacts the fluid, but it does not fully wet to dissolve in the fluid. The clumps of powdered media then float, stick to the surfaces of the chamber, and/or block influent or effluent ports in the chamber.

Thus, embodiments of the mixing apparatus 10 according to some embodiments help to achieve and enhance the vortex movement of the fluid by including one or more geometric flow aids, such as for example one or more cones along the lines of bottom cone 25 and upper cone 35, within the volume of the first chamber 12. It should be understood that while multiple cones are depicted, some embodiments contemplate a single cone flow aid, while in others, additional aids can be included. Thus, as liquid flows into the chamber via the influent ports 16, it is channeled into the chamber such that the swirling vortex motion is created immediately to establish the turbulent fluid motion for mixing the influent liquid with the contents of the first chamber 12. Furthermore, geometric flow aids further enhance mixing of the solid contents with the influent liquid by dispersing the solid and preventing it from sticking to or clumping at the bottom or the top of the first chamber 12. The geometric flow aids preferably comprise a geometric shape that have a decreasing diameter in a direction towards the center of the first chamber 12, so as to assist in the creation of the desired fluid flow vortex.

Figure 5A:
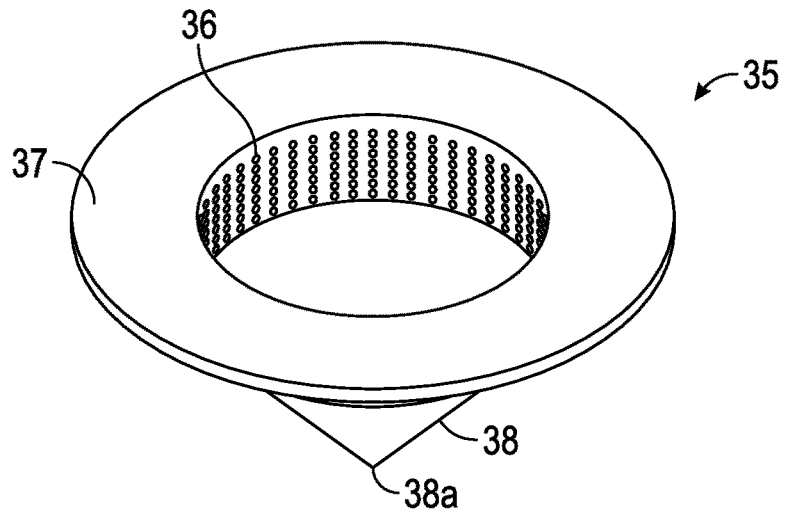
FIG. 5a is a top perspective view of a top cone of the mixing chamber according to one embodiment.
Figure 5B:
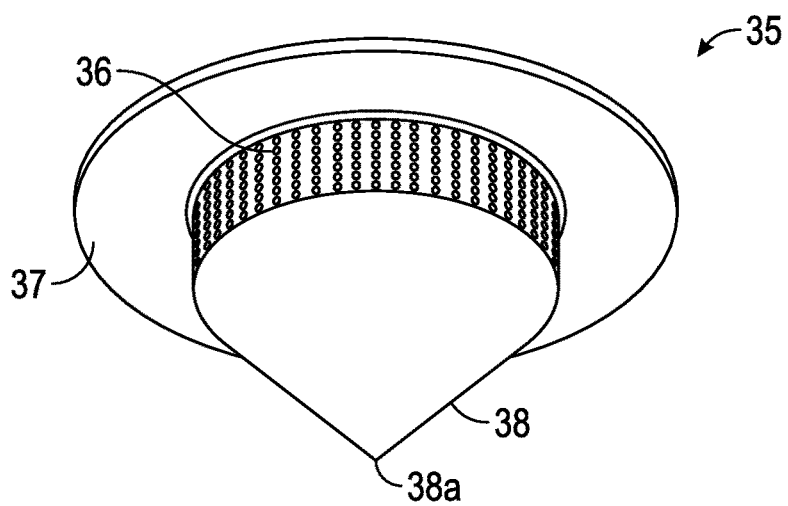

FIGS. 5A and 5B represent one embodiment of an upper geometric flow aid. In this embodiment, geometric flow aid is an upper cone 35. As described above, a geometric flow aid comprises a geometric shape that has a decreasing diameter in a direction towards the center of the first chamber 12. Accordingly, upper cone 35 has conical portion 38 with a decreasing diameter towards the center of the first chamber 12. Conical portion 38 is shown as terminating at cone tip 38a, but it is contemplated, in other embodiments, that conical portion my end before reaching a tip and would have a flattened end portion. Other shapes, besides a cone, are also contemplated for the geometric flow guide. Upper cone 35 also includes a plurality of pores 36 in a pored section, through which the fluid in the first chamber 12 can pass into the upper chamber 22. The pores 36 are configured with an appropriate diameter to prevent undissolved clumps of powdered media from entering into the upper chamber 22. Finally, upper cone 35 has a base portion 37 extending radially from a top edge of the pored section. Base portion 37 is configured to engage with support structure 34 of middle cap 31.

Figure 6:
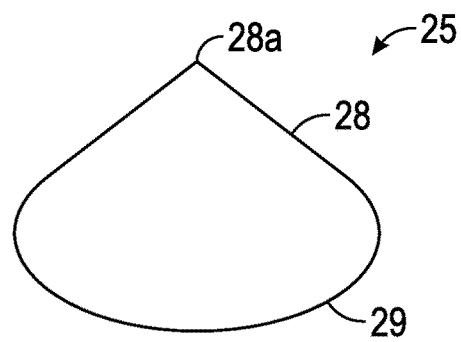
FIG. 6 is a top perspective view of a bottom cone of the mixing chamber according to one embodiment.

FIG. 6 represents one embodiment of a lower geometric flow aid. In this embodiment, geometric flow aid is a bottom cone 25. As described above, a geometric flow aid comprises a geometric shape that has a decreasing diameter in a direction towards the center of the first chamber 12. Accordingly, bottom cone 25 has conical portion 28 with a decreasing diameter towards the center of the first chamber 12. Conical portion 28 is shown as terminating at cone tip 28*a*, but it is contemplated, in other embodiments, that conical portion my end before reaching a tip and would have a flattened end portion. Other shapes, besides a cone, are also contemplated for the geometric flow guide. Bottom cone 25 also has a base edge 29 at the open end of the conical portion. Base edge 29 is configured to engage with support structure 24 of lower cap 21.

The interior of the first chamber preferably has a substantially cylindrical configuration. This further establishes a vortex guide for the liquid flow. Moreover, the cylinder diameter should complement the incoming fluid velocity. A first chamber diameter that is too large for a given influent flow will not support sufficient centrifugal force along its sides to maintain a vortex. Interior diameters that are too small could create excessive turbulence initially, but not form a vortex, thereby potentially resulting in inadequate mixing. The diameter of the first chamber has been found to optimally be proportional to its height. A height to diameter ratio greater than about 2.5:1 will typically not support the generation of a sufficiently strong vortex at influent flow rates of about 1-3 liters per minute. The substantially cylindrical shape in combination with the inlet velocity and the inlet angle thus combine to set up the desired vortex.

Alternatively, other chamber configurations which exhibit radial symmetry may also be used for the first chamber housing 22. For example, spherical, hemispherical, toroidal or the like may be selected.

Some embodiments can include additional mixing or turbulence components that can, for example, aid in the mixing process, or provide features that assist in breaking up clumps. Such aids can include protrusions (e.g., bristles or pegs) that extend radially toward the center of the chamber, or protrusions that attach to the cones, or to a center rod and extend radially outward. In some embodiments, certain mixing aids can be specifically excluded. For example, mixing components such as propellers, magnets, blades, and the like, can be specifically excluded from some embodiments.

Referring again to FIG. 3, the upper inner surface of the first chamber housing 22 may be coupled to, thereby enclosing the first chamber 12 with, the middle cap 31. A support structure 34 is preferably integrally molded together with or milled into the middle cap 31 to form a ledge or lip to support the first chamber 12 and the second chamber 14, as well as other components for engaging the first chamber 12 and the second chamber 14 and for allowing fluid flow between the chambers. Such components include the seals 32, 33, the top geometric flow aid, such as upper cone 35, and a filter disc 39. The assembly and components of the middle cap 31 are described in more detail below with reference to FIGS. 8A-8C.

The two chambers are preferably adjacent one another and separated from one another by middle cap 31. FIGS. 1-3 illustrate a preferred embodiment where first and second chambers 12, 14 are axially aligned in a water tight seal such that liquid enters the first, or lower chamber, and moves to the second or upper chamber passing through middle cap, including circular filter disc 39. In this construction, seals 32, 33 such as elastomeric O-rings are used to provide a tight seal between the upper and lower chambers. During manufacture, chemical A is preferably placed into first chamber 12 before the filter disc 39 has been put into place.

The upper chamber housing 42 is also preferably covered by upper cap 41, thereby enclosing the second chamber 14. A support structure 44 is preferably integrally molded together with or milled into the upper cap 41 to form a ledge or lip to sit upon the second chamber housing 42, as well as for receiving other components for engaging the second chamber housing 42 and for allowing fluid flow between the second chamber 14 and the effluent port 49. Such components include the seals 43, 45, 46, retaining plate 47, and a filter disc 48. The assembly and components of the upper cap 41 are described in more detail below with reference to FIGS. 9A-9D.

Figure 7:
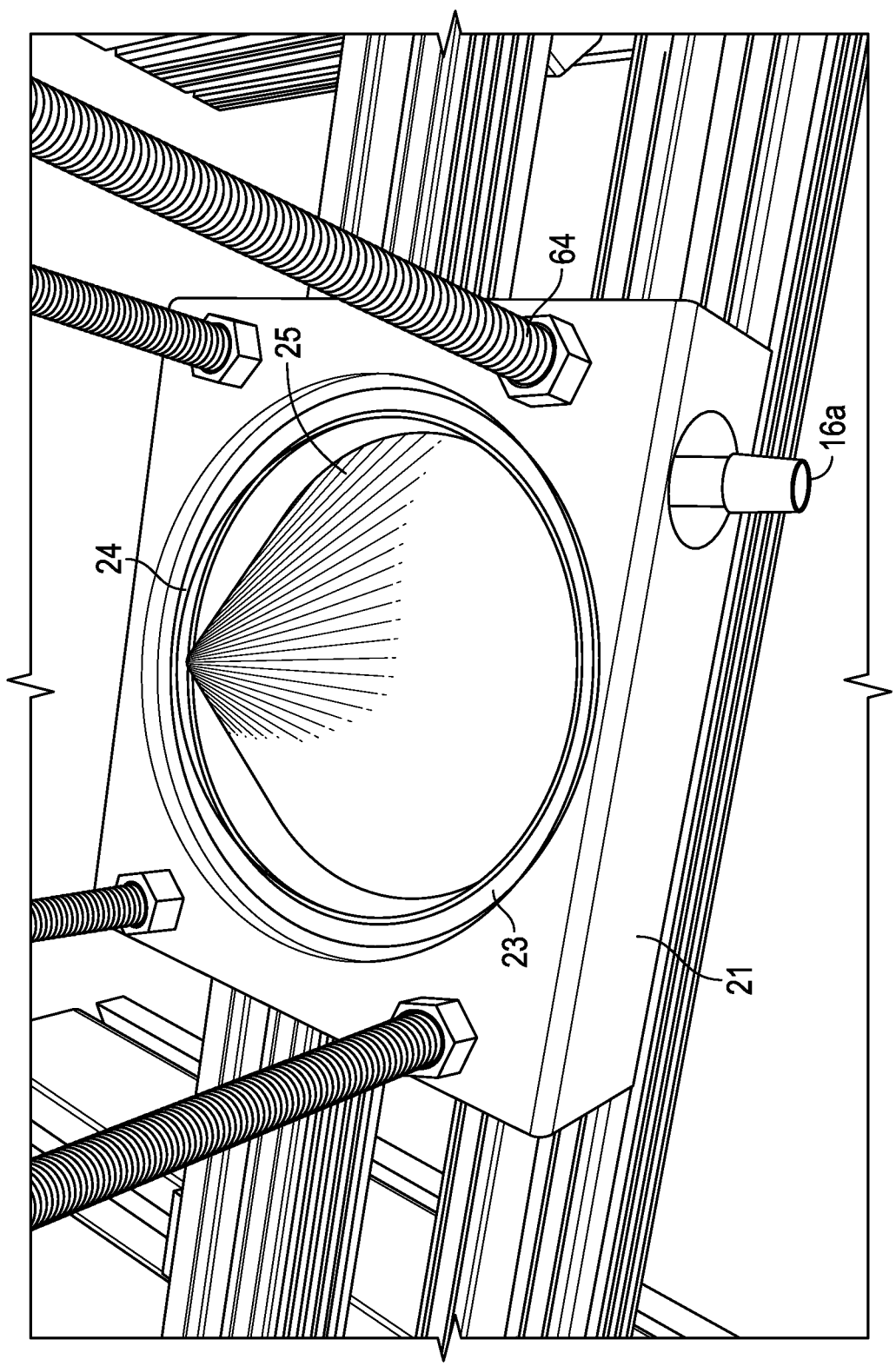
FIG. 7 is a top perspective view of a lower cap of the mixing chamber according to one embodiment of the present invention representing the assembly of the bottom cap and the bottom cone illustrated in FIG. 6.

FIG. 7 depicts the assembly of lower cap 21. As shown, lower cap comprises a base portion which includes influent port 16*a* and a support structure 24 formed therein which receives bottom cone 25. Positioned about the perimeter of bottom cone 25, and on support structure 24, is seal 23. The seal 23 is preferably an elastomeric O-ring but could be a gasket or other sealing device known to those with skill in the art. The seal 23 maintains a water-tight connection between the first chamber housing 22 and the lower cap 21.

In the embodiment shown, lower cap 21 also serves as the base for support rods 64. In the embodiment of FIG. 1, it is shown that two sets of support rods 64, 65 are used to separately secure the first chamber 12 and the second chamber 14, respectively. In the embodiment of FIG. 3, it is shown that a single set of rods 64 extend the full length of the mixing apparatus 10. In other embodiments, it is contemplated that the mixing apparatus 10 be sturdy enough to stand freely and securely without any support rods 64, 65.

Figure 8A:
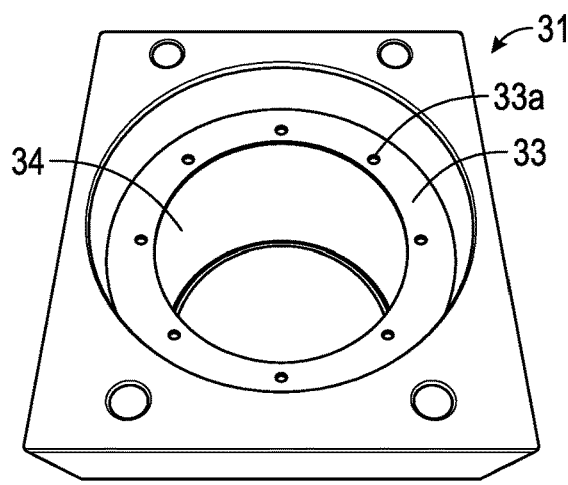
FIGS. 8a, 8b, and 8c are perspective views of the bottom of a middle cap of the mixing chamber according to one embodiment showing the assembly of the middle cap and the top cone illustrated in FIGS. 5a and 5b.
Figure 8B:
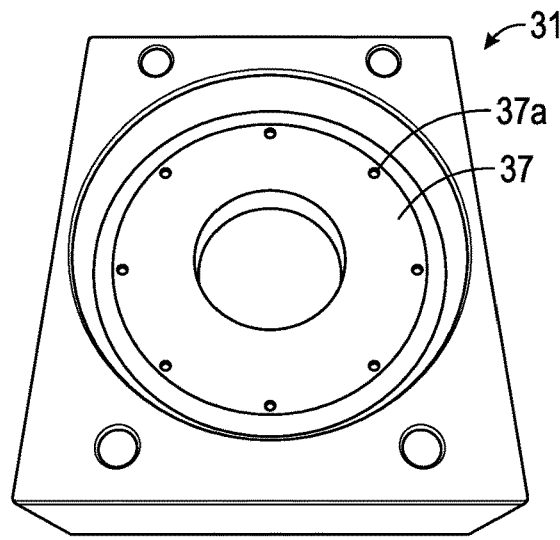
Figure 8C:
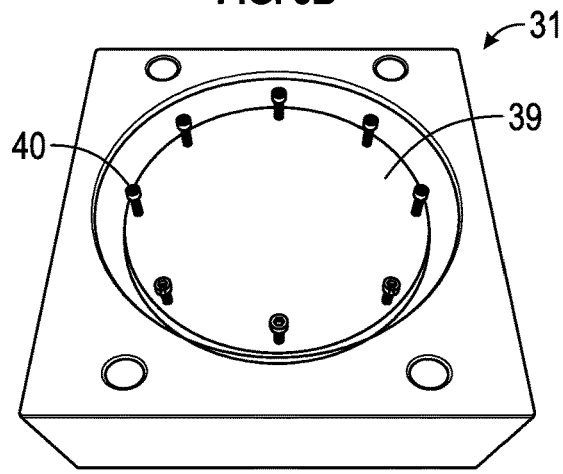

FIGS. 8A, 8B, and 8C depict the assembly of middle cap 31. As shown in FIG. 8A, middle cap 31 comprises a base portion with a central opening. Within the central opening is support structure 34, which is configured to receive seal 33 thereon. Seal 33 comprises a plurality of attachment holes 33*a*, each configured to receive a screw 40 therethrough to couple the elements of middle cap 31 together. As shown in FIG. 8B, the base portion 37 of upper cone 35 rest on the support structure 34 and the seal 33. Attachment holes 37*a* are aligned with attachment holes 33*a*. Finally, on top of the upper cone 35, the filter disc 39 is positioned. Filter disc 39 is secured to the middle cap 31 by positioning screw 40, or other attachment device through attachment holes 33*a* and 37*a* and into the support structure 34 of the middle cap 31.

The seal 33 is preferably an elastomeric O-ring but could be a gasket or other sealing device known to those with skill in the art. The seal 33 maintains a water-tight connection between the upper chamber housing 42 and the middle cap 31. The filter disc 39, while preferably made of microporous Porex™ plastic (Porex Technologies, Fairburn, Ga.), could additionally be made of porous polypropylene or polyethylene, glass, wool, micron meshing, or any of a variety of other inert substances having suitable compatibility with the solvents and powders to be used in the apparatus. Preferably, the filter material will have a sufficiently small pore size to prevent escape of the powdered media. In some embodiments, the filter has a porosity in the range of 30 to 200 microns. For the preferred application described herein, the filter preferably has a pore width of approximately 90 to 130 microns. The filter disc permits liquid passage into the second chamber but generally prevents the movement of undissolved solids from the first chamber 12 to the second chamber 14. Further undissolved solids trapped in the microporous filter are subsequently dissolved by the continued flow of fluid passing through the filter.

The first chamber housing 22 and the middle cap 31 are provided with a liquid tight seal 32 through the use of an elastomeric O-ring. The first chamber housing 22 can either slip fit into an annular recess on the cap 31 or threadably engage the base, to be coupled with the support structure 34. The housing can additionally be sealed to the cap 31 using adhesives, a heat seal or other means known in the art.

Figure 9C:
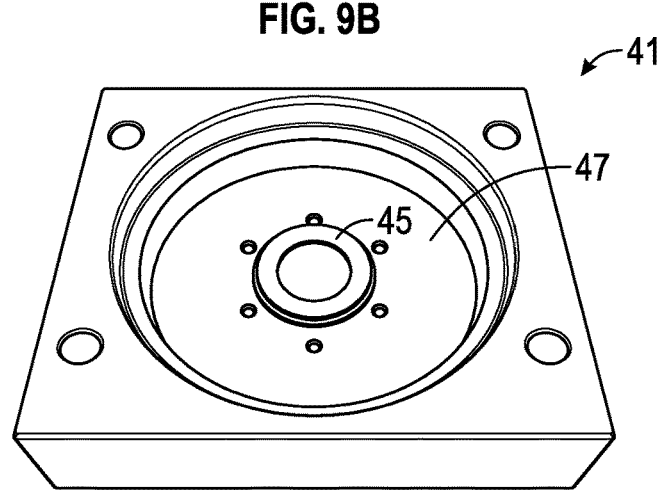
Figure 9D:
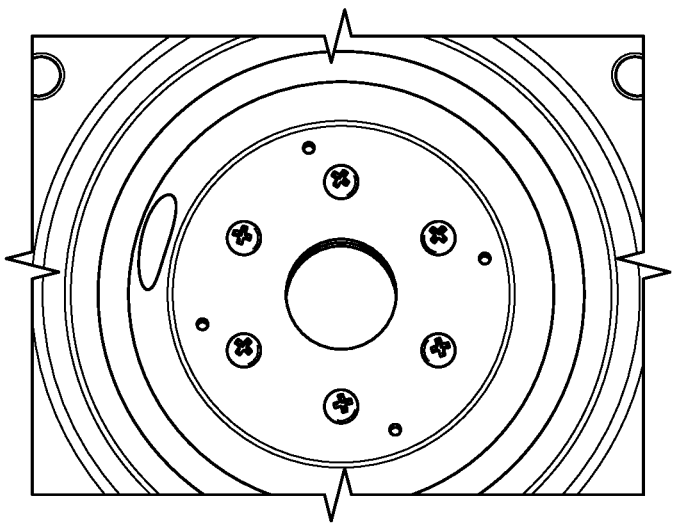

FIGS. 9A, 9B, 9C, and 9D depict the assembly of upper cap 41. The view in the figures is a bottom perspective view of upper cap 41. As shown in FIG. 9A, a seal 46 is placed to surround the exit aperture to effluent port 49. FIG. 9B depicts the placement of a filter disc 48, or effluent filter, over the top of seal 46 and the exit aperture. FIG. 9C depicts the placement of a second seal 45 on the inner face of filter disc 48. Finally, FIG. 9D shows placement of a retaining plate 47 covering seals 45, 46 and filter disc 48, which is held in place by attachment elements, such as screws 40, to the inner face of upper cap 41 via engagement apertures 41a in the upper cap. Seals 45 and 46 are preferably used to provide a water tight seal between the upper cap 41 and the upper chamber housing 42. Effluent filter 48 preferably sits at least about one-eighth of an inch from the interior surface of upper cap 41. This provides space for liquid containing chemicals A and B to pass through the effluent filter 48 and leave via effluent port 49.

Figure 10:
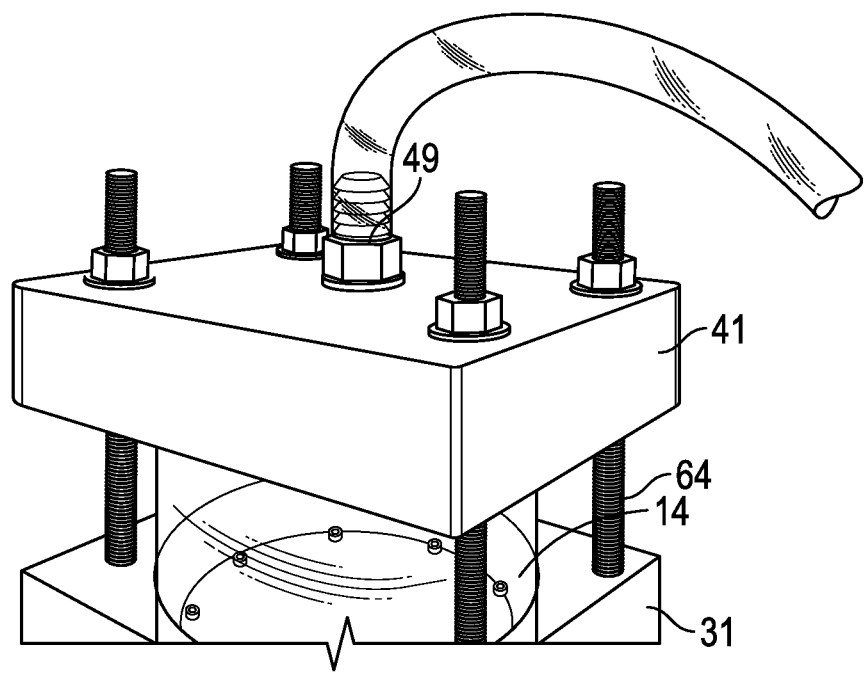
FIG. 10 is a perspective view of the top cap attached to an outlet tube according to one embodiment.
Figure 11:
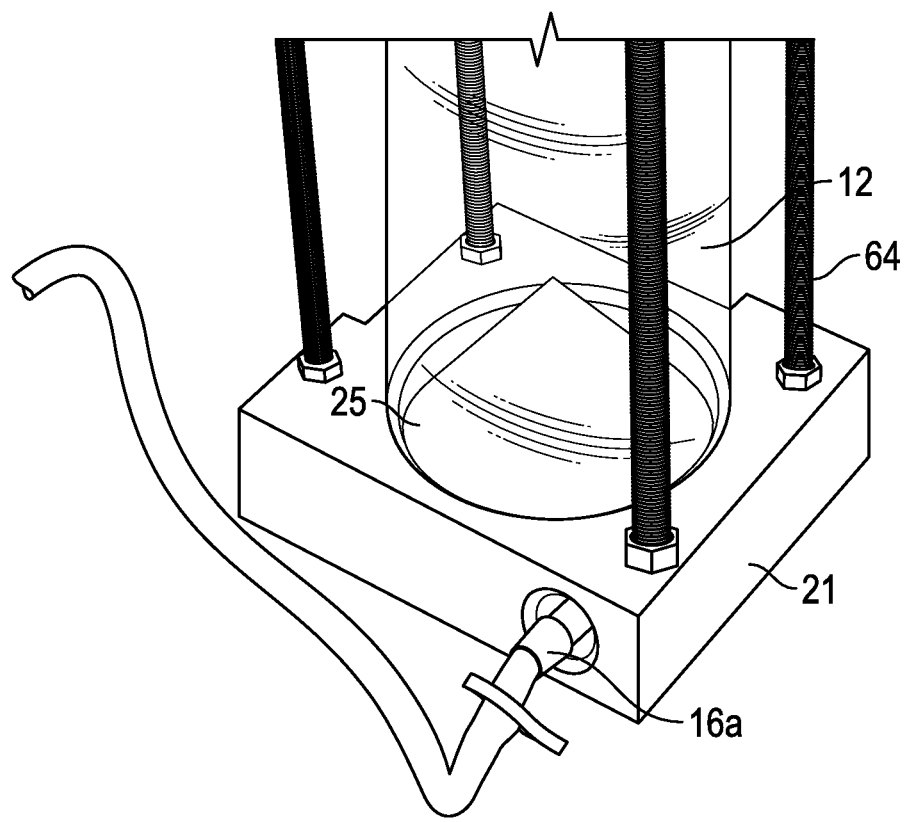
FIG. 11 is a perspective view of the bottom cap attached to an inlet tube according to one embodiment.
Figure 12:
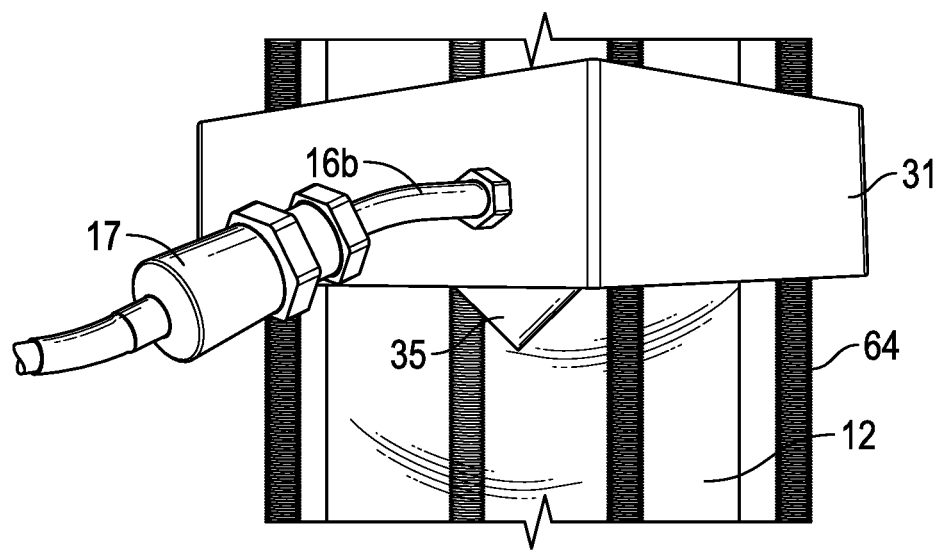
FIG. 12 is a perspective view of the middle cap attached to an inlet tube and a pressure transducer according to one embodiment.

As shown in FIG. 10, effluent port comprises a hose barb connector, to which a flexible hose is attached to move fluid from the mixing apparatus 10 to a media collector, such as receptacle 50. As shown in FIGS. 11 and 12, hoses are also preferably affixed to the influent ports 16a, 16b and may be locked in place via a hose barb connector. In a preferred embodiment, standard flexible laboratory tubing of diameter sufficiently large such that the tubing will pass over the neck of the hose barb and sufficiently small that the tubing seals over the hose barb nozzle is employed to direct the incoming fluid stream to the mixing chamber or the outgoing stream to the receptacle 50. The other end of the influent flexible tubing is preferably applied directly to a source of fluid. In the preferred culture media application, the influent ports 16a, 16b are placed in fluid communication with a distilled deionized water ($ddH_2O$) source having an adapted nozzle such as is found in most scientific laboratory $ddH_2O$ faucets. Other tubing materials, nozzle adapters, and pumps may be required for use with other water sources or liquid solvents. Any of the ports, or other passageways of the mixing apparatus 10, may include a pressure transducer 17, as shown in FIG. 12. The pressure transducer can be used to quantify and monitor the pressure in the system and make any changes that may be necessary to preserve the functionality of the system.

Flexible tubing for providing communication between system components may be sterilized, such as by autoclave or gamma irradiation, and assembled together at the point of manufacture. It is additionally preferred that a sterile receiving receptacle be supplied with the apparatus. The sterile receiving receptacle could be glass, plastic, or metal and could be preformed or flexible. In a preferred embodiment, the receiving receptacle comprises a sterile flexible bag such as the Media Manager Product (Irvine Scientific, Santa Ana, Calif.)

In a preferred embodiment, the mixing chambers and caps are made of a nonreactive plastic polymer such as polycarbonate. Alternatively, the caps and chambers could be molded from other plastics including polysulphone. Other materials include polystyrene, polyethylene, polycarbonate, plexiglass, lucite, polypropylene, a metal alloy, or glass. Preferably, the chamber housings 22, 42 will be transparent to enable visual observation of its contents or the progress of the mixing cycle.

Generally, the mixing apparatus 10 is preferably made of materials that are appropriate for the cell culture environment, such as non-toxic, medical grade plastics or other non-toxic materials that will not contaminate the media. In current designs, stainless steel may be used, however there is a need for single use systems. Accordingly, the materials chosen must be relatively inexpensive, while being appropriate for cell culture environments, to keep material and manufacture costs low for single use products.

In a preferred application, the mixing apparatus is used to prepare tissue culture media. It is contemplated that the mixing chamber will be provided prefilled with powdered media in a variety of unit volume sizes. For example, mixing chamber sizes to accommodate the preparation of 1 liter (L), 10 L, 20 L, 50 L, and as large as 100 L or larger final tissue culture media volume are contemplated. Increasing amounts of powder in the lower chamber will require increased cylinder height and/or diameter to generate a vortex of sufficient size so as to maintain the powder in motion within the vortex until it dissolves. In addition, larger sizes may require a pump on the influent line to generate sufficient influent flow to sustain a vortex. Therefore it is contemplated that each apparatus be specifically designed to complement the final volume of product to be prepared.

Testing has determined that a powder volume greater than about 50% of the chamber volume for the powdered culture media application results in poor vortex mixing and inefficient liquid reconstitution. Testing has additionally determined that during operation of the mixing apparatus herein disclosed, improved reconstitution of the powder in the liquid is achieved by interrupting the inflow occasionally for approximately five seconds. Interrupting the flow temporarily releases pressure within the chamber thus allowing clumps of powder to draw fluid to their interior.

In addition, pressure pulsing can be applied to the mixing apparatus, to improve reconstitution by temporarily closing the outlet valve at the effluent port. This allows pressure to build up in the chambers while the valve is pinched. When the valve is released and pressure quickly drops, the clumps of powder that may have formed in the liquid are pulverized. This pressure pulsing can be implemented manually by pinching the outlet tubing, or by incorporating a pinch valve at the effluent port into the design.

A precalibrated receptacle 50 can be used to determine the end point of media preparation. Alternatively, a predetermined volume of liquid can be pumped through the system or a flow meter/accumulator can be used to monitor the volume of the finished product. It is additionally contemplated that the final volume of the liquid product can be determined by weight. The receiving receptacle is placed on a scale and the receptacle is filled until the final weight of the end product is achieved.

It is important for the effective operation of the apparatus that the culture media powder remain relatively dry prior to use. Hygroscopic powders tend to clump under humid conditions and reconstitution becomes difficult. It is therefore contemplated that the commercial product comprising a mixing apparatus system with powder be packaged under vacuum and/or preferably be provided with a desiccant.

It is additionally contemplated that the apparatus disclosed herein has a number of other commercial or industrial applications. For example, many liquid pharmaceuticals are prepared in the hospital pharmacy with some frequency and quantity. Saline solutions, alimentary preparations, imaging reagents, dyes, sterilization solutions and anesthetics are reconstituted as liquids. Premeasured aliquots provided ready for reconstitution such as contemplated by the disclosed technology can provide an advantage over the current art.

Alternative applications include, but are not limited to, preparation of pesticides, fertilizers, any of a variety of beverages commonly prepared from powder such as milk, iced tea, etc. which could all be reconstituted using the disclosed technology according to some embodiments. It is further contemplated that the liquid solvents employed can be water, alcohols or other organics. The solubility characteristics, the solvent to be used, the amount required and the chemical interactions between the solvent and the reconstituted chemicals will serve to provide guidelines for the size of the mixing chamber and the choice of materials for the components.

A variety of modified forms of the technology can be constructed for different end uses. For example, the diagrams depict a preferred embodiment wherein the first mixing chamber is coaxially aligned beneath the second chamber and separated by a microporous circular filter disc. In this embodiment the upper and lower chambers both have a cylindrical shape and the circular filter disc follows the shape of the chamber casing. As noted, the lower chamber preferably has a generally cylindrical shape and geometric flow aids in order to facilitate rotational fluid velocity of sufficient turbulence.

However, it is not necessary for the upper chamber to have a cylindrical shape. Other shapes for the second chamber as well as for the microporous filter disc are contemplated. The second chamber could be rectangular, ovoid or essentially spherical. Further, the first and second chambers do not necessarily have to be positioned on top of one another. It is contemplated that the two chambers could be disposed side by side or remote from one another and in fluid communication by way of silicone, glass or other conventional tubing.

Figure 13:
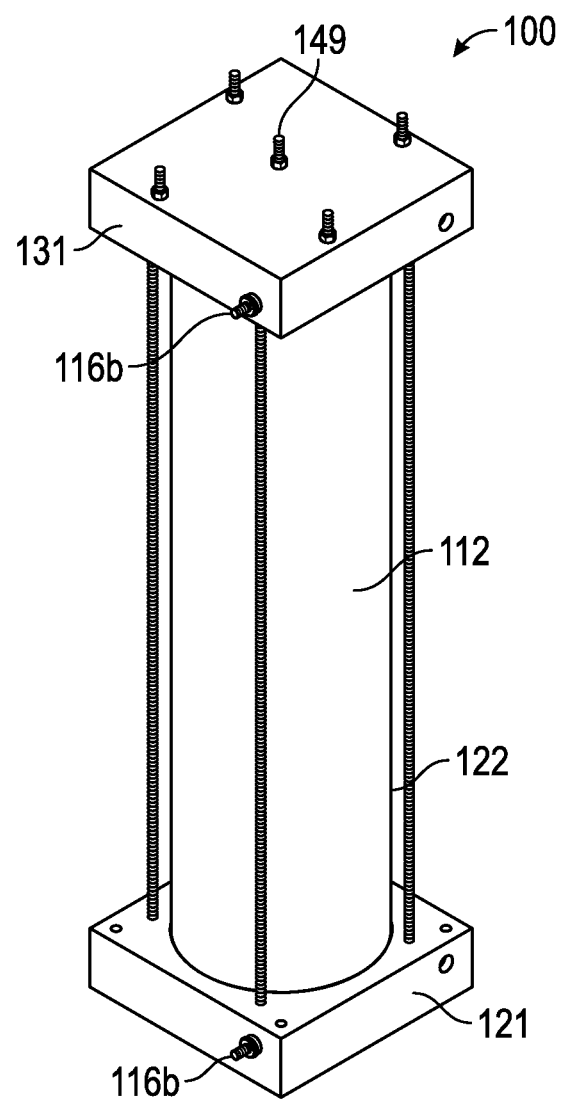
FIG. 13 is a schematic representation of a single-chamber mixing apparatus in accordance with one embodiment.

Furthermore, it is contemplated that the mixing apparatus include only one chamber. A mixing apparatus 100 according to a second embodiment is shown in FIG. 13. In this embodiment, only first chamber 12 is needed. Both the powdered media and the secondary additive, such as sodium bicarbonate, can be provided to the first chamber 12 together. Therefore, only one chamber is needed to dissolve the solid in the fluid. Accordingly, mixing apparatus 100 includes a lower cap 121, similar to lower cap 21 described above, chamber housing 122, and upper cap 131, which is similar to both middle cap 31 and upper cap 41. In particular, upper cap 131 includes influent port 116b as well as effluent port 149, and thereby serves to provide the fluid to the chamber 112 and deliver mixed fluid to a media receptacle. Other details associated with mixing apparatus 10 can be applied similarly to mixing apparatus 100.

This technology according to some embodiments provides a closed, self-contained mixing system to reconstitute a unit dose of chemical into a known final liquid volume. The discussion provided above serves to point out those design features that can be modified to adapt the disclosed apparatus for a wide range of applications. The desirability of specific influent port angles, position, number and diameter along with chamber dimensions, fluid pressure and a need for external turbulence generators are design features which will be able to be readily optimized by one of skill in the art for the reconstitution of a given formulation.

While the preferred embodiments described herein employ powdered chemicals, it is contemplated that the mixing apparatus can work equally well for the reconstitution of a concentrated liquid or a sequential combination of liquid and powder.

Thus, some embodiments of the technology disclosed herein provide a method and apparatus for the single step preparation and, if required, sterilization of a given chemical. The system is closed, therefore handling is minimized. All chemicals are premeasured so employee efficiency is maximized. The closed system additionally permits a complex sequential or multicomponent reconstitution and sterilization process to be performed in a convenient location without the risk of contamination and with minimal variation in end product due to technician error or batch variation. In addition, the combination of a closed system with desiccant under vacuum yields prepackaged units having a relatively long shelf life and improved tolerance to temperature change over the corresponding liquid product.

The entire content of U.S. Pat. No. 5,470,151 is herein incorporated by reference in its entirety.

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or aspects of the technology should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the terms "comprising" and "having" should, respectively, be interpreted as "comprising at least" and "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an." In general, "a" and/or "an" should be interpreted to mean "at least one" or "one or more"; the same holds true for the use of definite articles used to introduce claim recitations. Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The technology disclosed herein has numerous applications and while particular embodiments of the technology have been described in detail, it will be apparent to those skilled in the art that the disclosed embodiments may be modified given the design considerations discussed herein. Therefore, the foregoing description is to be considered exemplary rather than limiting, and the true scope of the invention is that defined in the following claims.

What is claimed is:

1. A method of reconstituting a powdered cell culture media, the method comprising:
    providing a mixing apparatus, comprising:
        at least one fluid chamber;

a first cap enclosing a lower portion of the fluid chamber;

a second cap enclosing an upper portion of the fluid chamber;

an influent port in at least one of the first cap and the second cap;

a geometric fluid flow aid coupled to the first cap and extending away from the first cap in a direction towards a center of the fluid chamber, wherein the geometric fluid flow aid comprises a geometric shape having a decreasing diameter in the direction towards the center of the fluid chamber;

a filter material associated with the second cap, wherein the filter material is used to keep the powdered cell culture media inside the fluid chamber until dissolved; and an effluent port in the second cap;

providing a powdered cell culture media to the fluid chamber, prior to introducing fluid to the chamber;

introducing fluid to the chamber through the influent port, wherein the influent port is tangentially oriented relative to an inner wall of the fluid chamber to thereby cause the fluid to follow the wall of the fluid chamber in a circular motion;

creating a vortex flow in the fluid chamber by introducing fluid at a sufficient flow rate;

enhancing the vortex flow with the geometric fluid flow aid by further channeling the fluid around the wall of the fluid chamber, around the geometric flow aid; and continuing to introduce fluid to the chamber and collecting reconstituted fluid that exits the chamber through the effluent port.

2. The method of claim 1, wherein the mixing apparatus further comprises a second fluid chamber, the second fluid chamber being provided with a powdered additive substance, and wherein the fluid exits the first chamber and moves into the second chamber to reconstitute the additive substance.

3. The method of claim 1, wherein the mixing apparatus further comprises a second influent flow port in the other of the first cap and the second cap, and wherein the method further comprises introducing fluid to the chamber through the second influent port.

4. The method of claim 3, wherein fluid is introduced through the influent port and the second influent port concurrently.

5. The method of claim 3, wherein the introduction of fluid alternates between the influent port and the second influent port.

6. The method of claim 3, wherein the influent port is in the second cap and the second influent port is in the first cap, and wherein the method further comprises introducing fluid through the influent port in the second cap until fluid has partially filled the fluid chamber and then introducing fluid through the second influent port in the first cap.

7. The method of claim 3, wherein the first and the second influent ports are positioned on the same vertical plane.

8. The method of claim 3, wherein the first and the second influent ports are tangentially oriented relative to an inner wall of the fluid chamber.

9. The method of claim 1, wherein the mixing apparatus further comprises a second geometric fluid flow aid, wherein the first geometric fluid flow aid is positioned at a bottom of the fluid chamber and the second geometric fluid flow aid is positioned at the top of the fluid chamber.

10. The method of claim 9, wherein the first and the second geometric fluid flow aids are substantially cone-shaped.

11. The method of claim 1, further comprising:

decreasing the diameter of an exit at the effluent port, thereby increasing the pressure inside the chamber; and returning the diameter to the normal diameter, thereby quickly decreasing the pressure inside the chamber, and causing a pulverization of clumps of powdered media in the fluid.

12. The method of claim 1, wherein the powdered cell culture media is formulated with the inclusion of sodium bicarbonate.

13. The method of claim 1, further comprising determining the end point of media preparation by collecting reconstituted fluid in a precalibrated receptacle.

14. The method of claim 1, further comprising determining the end point of media preparation by flowing a predetermined volume of liquid through the mixing apparatus.

15. The method of claim 1, further comprising determining the end point of media preparation by monitoring the volume of reconstituted fluid using a flow meter or accumulator.

16. The method of claim 1, wherein the powdered cell culture media is provided pre-loaded in the mixing apparatus.

17. The method of claim 1, further comprising disposing of the mixing apparatus after a single use.

18. The method of claim 1, wherein the filter material is made from porous polypropylene or polyethylene.

19. The method of claim 1, further comprising filtering the reconstituted fluid using a sterilization filter.

20. The method of claim 19, further comprising using a hydrophobic vent filter positioned between the effluent port and the sterilizing filter to allow air that is entrained in dissolved medium to vent.

\* \* \* \* \*